(12) United States Patent
Kuo

(10) Patent No.: US 6,902,337 B1
(45) Date of Patent: Jun. 7, 2005

(54) DENTIFRICE DISPENSING ELECTRICAL TOOTHBRUSH

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 4 days.

(21) Appl. No.: 10/873,434

(22) Filed: Jun. 23, 2004

(51) Int. Cl.[7] .................. A46B 11/02; A46B 11/04; A61C 1/10; A61C 1/07
(52) U.S. Cl. .................. 401/188 R; 401/278; 401/270; 433/84; 433/85; 433/89; 433/122; 433/131
(58) Field of Search .................. 401/187, 188 R, 401/270, 278, 279; 15/23, 24, 28, 29; 433/84, 433/85, 89, 118, 122, 131

(56) References Cited

U.S. PATENT DOCUMENTS

| | | |
|---|---|---|
| 5,640,735 A | 6/1997 | Manning |
| 6,164,967 A * | 12/2000 | Sale et al. .................. 433/80 |
| 6,434,773 B1 | 8/2002 | Kuo |
| 6,735,803 B2 | 5/2004 | Kuo |

* cited by examiner

Primary Examiner—David J. Walczak

(57) ABSTRACT

A dentifrice dispensing electrical toothbrush using a replaceable dual-channel brush head. The dual-channel brush head has a first channel for housing a drive shaft for bristle oscillation and a second channel for dispensing the dentifrice material. The brush head is mounted on the dual-channel connector of the brush handle which contains a drive mechanism and a pumping mechanism that dispenses dentifrice material from a cartridge in the handle. A manual dispensing configuration uses an external rubber button and an electrical dispensing configuration uses a rotary solenoid for actuating an internal rubber button that applies pumping pressure to the dentifrice material. The latter benefits arthritis sufferers, as no external squeezing action is required.

8 Claims, 5 Drawing Sheets

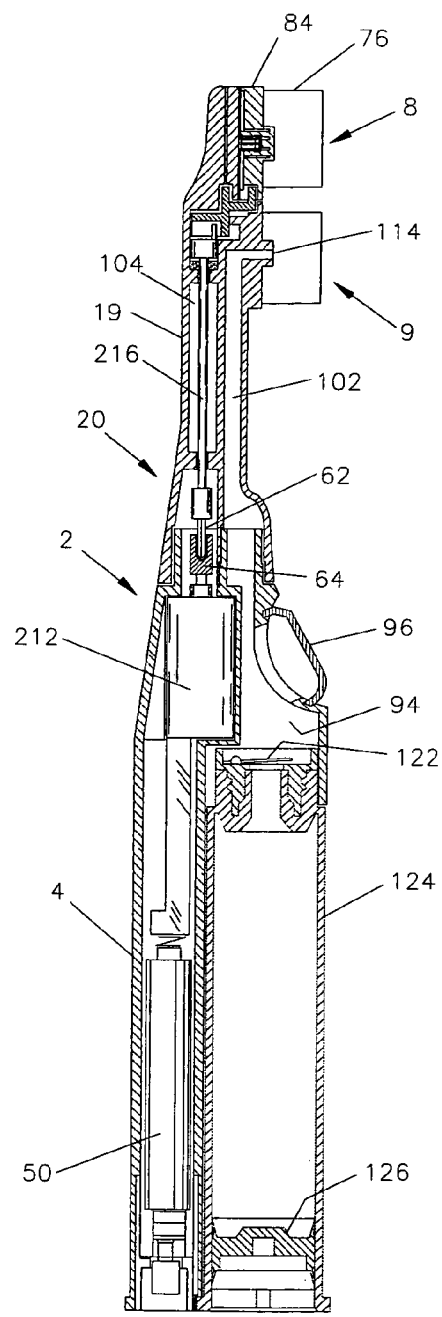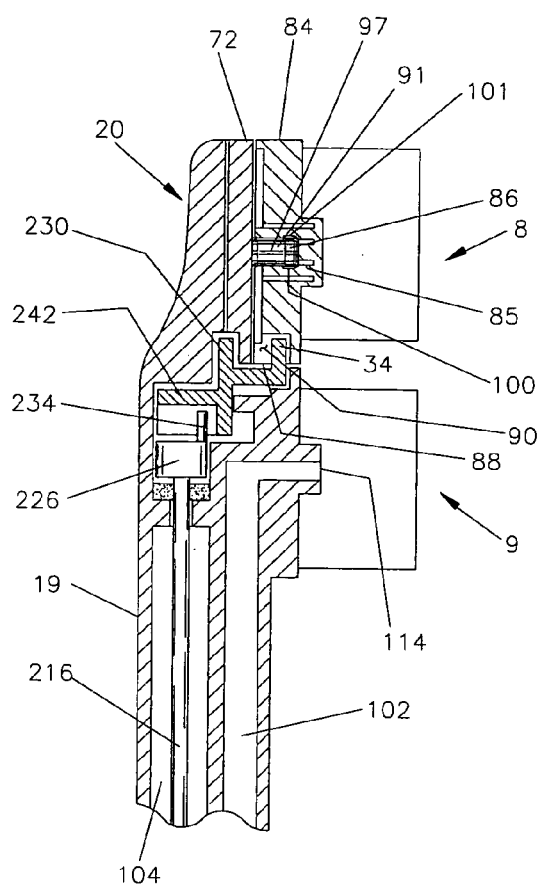
Fig. 1a
Fig. 1b

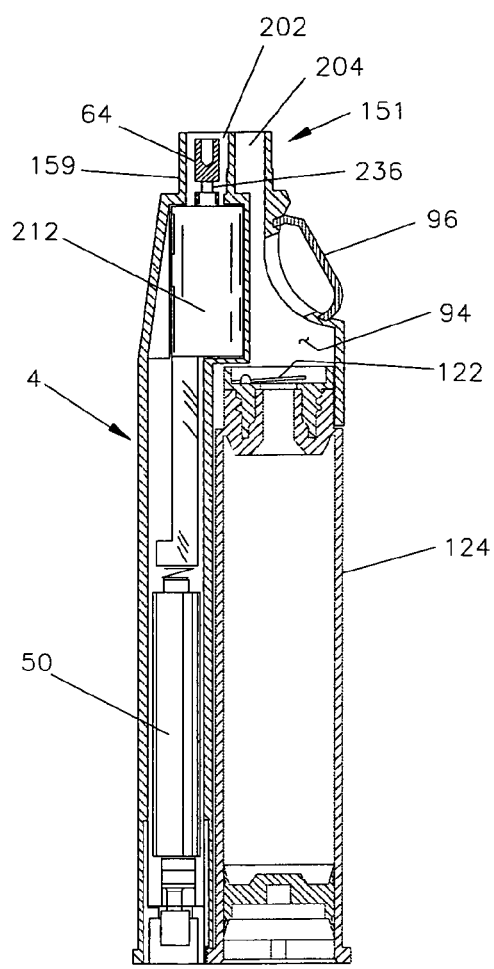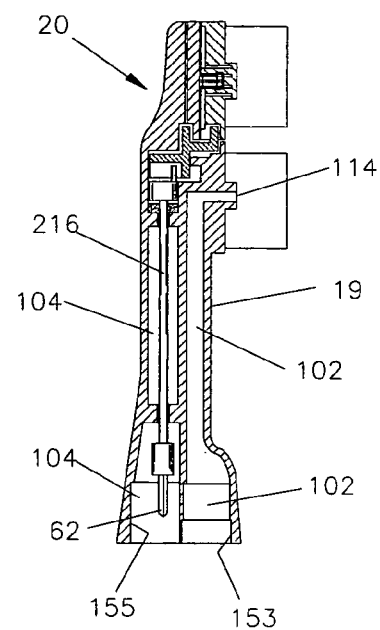
Fig. 3a
Fig. 3b

DENTIFRICE DISPENSING ELECTRICAL TOOTHBRUSH

BACKGROUND OF THE INVENTION

It has been recognized that an electrical toothbrush is more effective in removing plaque and preventing gum disease than a conventional manual toothbrush. It is also well known that squeezing on a toothpaste tube for dispensing toothpaste presents a significant challenge to severe arthritis suffers as well as the visually impaired. Thus an electrical toothbrush integrated with a toothpaste dispensing pump is a necessity for the physically challenged and also desirable for the convenience of general consumers. For long service life, all wearable parts need to be included in one replacement unit. For the ease of replacement, it is desirable to have a failure-free single-step in the mounting of the replaceable brush head on the toothbrush handle which contains driving components and a pumping mechanism. For the ease of operation for the physically challenged, it is desirable simply to press on an electrical switch for automatic dispensing of dentifrice material to the top of the bristles. It is the objective of the present invention to achieve the above desirable features in one dentifrice-dispensing electrical toothbrush.

(1) Field of the Invention

The present invention relates to an dentifrice dispensing electrical toothbrush using a replaceable brush head having dual channels for housing a drive shaft for bristle oscillation and a flow path for dispensing toothpaste.

(2) Related Art

U.S. Pat. No. 5,640,735 provides a water-flow powered toothbrush using a gear train assembly to accomplish controlled rotation of a plurality of gear driven bristle tufts. Separated from the water-flow drive, the toothbrush mechanism incorporates a flushing water supply passage for the circulation of clean water through a gear system thereby accomplish continuous cleaning of the gear train during tooth brushing activity. The brush head and housing structure define flushing water inlet and outlet passages which are in communication with the internal gear chamber of the brush head. The brush head is also provided with a water outlet valve that is forced to open by excessive water pressure when a user covers the water outlet port by a finger. Although its replaceable brush head contains a drive shaft and flow channels, its flow passage mechanism is for the circulation of cleaning water only. It is not applicable to the one-way dispensing of toothpaste, which requires a single outlet flow channel and one-way check valve to block any returning flow of toothpaste into a pumping chamber.

For low cost replacement of brush unit of a dentifrice dispensing electrical toothbrush, U.S. Pat. No. 6,434,773 by Kuo uses a replaceable brush cradle unit containing two bristle elements with no drive shafts. The replaceable brush cradle unit is detachably fastened to the drive head of a neck containing a drive shaft and a flow channel which are integrally attached to the toothbrush handle. The dentifrice material is pumped from the cartridge in the handle to the spout opening at the base of one of the bristle elements. The two bristle elements are engaged with the posts of the drive head in a manner that allows them to free to oscillate by a snap-on retention cradle. They are easily detached and replaced without replacing the drive shaft. Rotary motion from a motor is converted to oscillatory motion with either a cam assembly or an off-center shaft extension for engaging the drive notches of the bristle elements. The replacement method has disadvantages. Although only the bristle elements and the retention cradle are replaced, the posts supporting the free rotation of the brush elements are wearable but they remain on the permanent drive head. A worn post can cause wobbling of oscillating bristle element and excessive noise that results in reduced service life of the toothbrush. Furthermore, the mounting of the replaceable cradle unit on the drive head requires manual insertion of the notches of the bristle elements on top of the drive tab in the drive head. As the drive tab stops at a random position, aligning the two notches against the drive tab presents a significant challenge for the user.

To achieve a compact brush head profile, U.S. Pat. No. 6,735,803 by Kuo utilizes a linkage for converting a rotary motion of the drive motor to a planar motion in imparting the oscillation of a rotary bristle unit in an electrical dentifrice-dispensing toothbrush. Similar to the above U.S. Pat. No. 6,434,773, the replaceable bristle unit does not contain a drive shaft. The drive shaft is included in a non-detachable neck which is integrally connected to the handle. The replaceable bristle unit consists of a rotary bristle element and a stationary bristle element. The latter has an opening for the flow of dentifrice material through the drive head. The bristle unit is snap-on latched to the side walls of the drive head. The linkage is used to convert the rotation of the drive shaft to a planar oscillation that enables a compact drive head configuration. The dentifrice dispensing is accomplished by using a rotary solenoid for actuating an internal elastic compressible button that applies pumping pressure to the dentifrice material. The mechanism of the replaceable bristle unit as describes has the same disadvantage of requiring a special effort in aiming at the position of the linkage arm for the insertion of the notch of the rotary bristle unit. As the mounting of the rotary bristle unit is one-way and non-detachable, any misalignments of the notch on the linkage arm can cause damage to the drive mechanism.

SUMMARY OF THE INVENTION

The present invention provides a dentifrice dispensing electrical toothbrush that uses a replaceable brush head having dual channels for housing a drive shaft for bristle oscillation and a flow path for dispensing toothpaste. A manual dispensing configuration utilizes an external rubber button for applying a pumping force for dispensing the toothpaste while an electrical-mechanical dispensing configuration uses an internal rubber button and an electrical actuator means for doing the same.

In the dual-channel brush head, one channel houses the first drive shaft and a separate channel functions as part of the flow path of the pumped dentifrice material. The electrical dispensing mechanism includes a switch, a rotary solenoid, and a plunger in contact with a resilient rubber button. The activation of the switch causes the rotary solenoid to lift the plunger to press on the rubber button to force dentifrice material to flow to the top of the bristles. Through a control mechanism, de-activation of the switch causes these components back to their original home positions and accordingly the follower inside the cartridge advances to keep the dentifrice material in a packed condition for next pumping action.

The essential components of the dentifrice dispensing electrical toothbrush include 1) a handle which serves as a housing for a motor, batteries and a toothpaste cartridge; 2) a replaceable dual-channel brush head having a rotary bristle element and a stationary dispensing bristle element with a spout opening; 3) a dual-channel connector on the handle; 4)

a drive coupling mechanism; 5) an electrical actuation mechanism including a switch, a rotary solenoid, and a plunger.

BRIEF DESCRIPTION OF THE DRAWINGS

FIG. 1a is a cross section view of a drive mechanism for a dentifrice dispensing electrical toothbrush having a replaceable dual-channel brush head.

FIG. 1b is an enlarged cross section side view of the drive mechanism and the spout opening in the brush head of FIG. 1a.

FIG. 2 is an illustration of the engagement between two drive shafts, bristle elements and an oscillation linkage shown in FIG. 1a.

FIG. 3a is a cross section view of the handle of dentifrice dispensing electrical toothbrush showing exposed dual-channel connector.

FIG. 3b is a cross section view of a replaceable dual-channel brush head detached from the dual-channel connector.

DETAILED DESCRIPTION OF PREFERRED EMBODIMENTS

Figure 2:
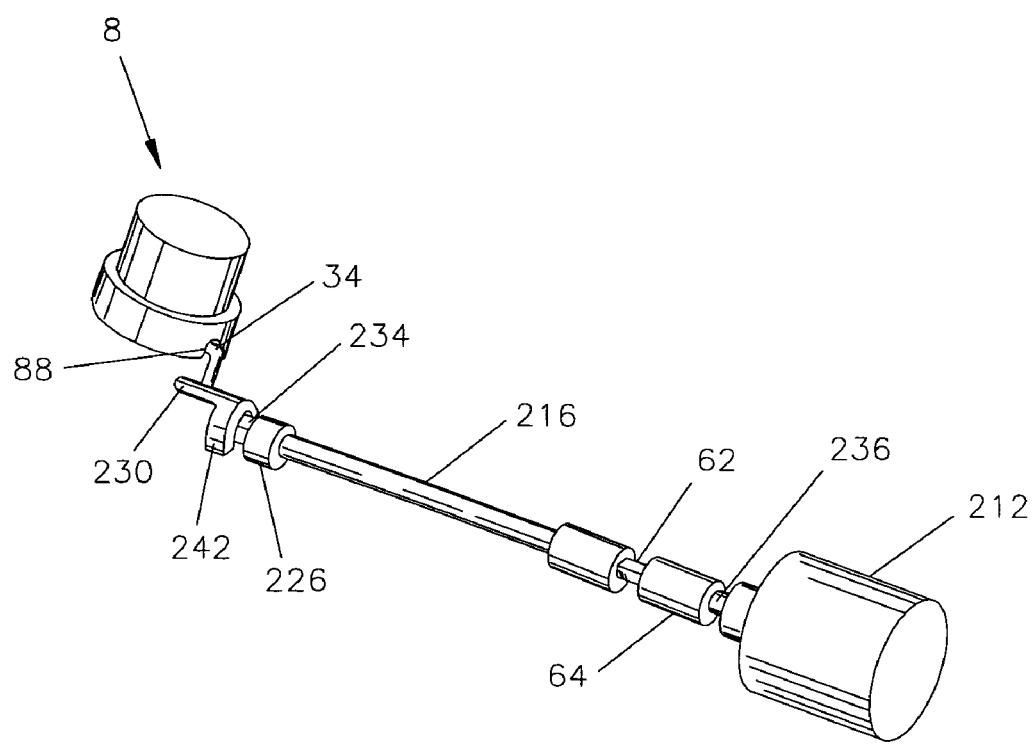

Throughout the following detailed description, the same reference numerals refer to the same elements in all figures.

A dentifrice dispensing electrical toothbrush of the present invention has a replaceable dual-channel brush head and a handle having a dual-channel connector. The dual-channel brush head has a channel for housing a drive shaft for the oscillation of the first rotary bristle unit and a separate channel for the flow of dentifrice material to the top of the second bristle unit. The dual-channel brush head is detachably mounted on the dual-channel connector, which contains a drive shaft driven by a motor and a flow channel in communication with the pumping chamber for dispensing the dentifrice material to the second bristle unit from a cartridge inserted in the handle serving as reservoir for the dentifrice material.

Referring to FIG. 1a, a dentifrice-dispensing electrical toothbrush 2 has handle 4 with dual-channel connector and replaceable brush head 20. The latter is shown separately in FIG. 3b and also partially shown in an enlarged view in FIG. 1b. First bristle unit 8 is mounted on post 86 and second bristle unit 9 has spout opening 114. The first bristle unit 8 is driven by cam linkage 242 attached to the top end of first drive shaft 216 in the replaceable brush head 20, which is detachably engaged with second drive shaft 236 driven by motor 212 powered by the battery in the handle 4.

Dentifrice cartridge 124 having follower 126 is also housed within handle 4. Dentifrice material (not shown) is pumped from pump chamber 94, through first flow channel 102 and spout opening 114, to bristle unit 9. A pumping force is supplied to chamber 94 by depression of elastic compressible button 96 that closes the one-way valve 122. As the elastic compressive button 96 is released to restore to its original free position the follower 126 in the cartridge moves forward under a vacuum force to compact the dentifrice material.

The structure and function of the dentifrice dispensing electrical toothbrush of the present invention are described in details as follows.

Further shown in FIG. 1a and FIG. 1b, a plurality of bristles 76 are attached to the top surface of base 84 of first bristle unit 8. Drive notch 90 is appended to side wall 88 of bristle base 84. The underside of bristle base 84 has split bushing walls 85 which are shaped to mate with post 86 of platform 72. Drive notches 90 of first bristle unit 8 accommodates drive rod 34 such that when drive rod 34 is positioned in drive notch 90, the oscillating motion of drive rod 34 causes first bristle unit to freely oscillate on post 86. The mechanism for the oscillation motion will be described in later sections. The mounting of a rotary bristle unit on a stationary post for free rotation and its one-way engagement for preventing detachment of the rotary bristle unit from the post has been described in prior art. A preferred embodiment as disclosed in U.S. Pat. No. 6,735,803 by Kuo is briefly described below.

The one-way engagement of bristle base 84 of bristle unit 8 on post 86 is enabled by the mounting of two half-circle-shaped split bushing walls 85 on the underside of bristle base 84 on two half-circle-shaped split shaft walls 91 of post 86. Gaps (not shown) between split walls 85 allow wall deflections apart from each other while gaps 97 of post 86 allow for deflections of adjacent split walls 91 toward each other. All the split walls are of cantilever configuration for flexibility for the mounting of bristle unit 8 on post 86. For preventing disengagement, post 86 has retention rim 100 and the flexible bushing has annular groove 101 at corresponding mating positions. The diameter of retention rim 100 of post 86 is smaller than the diameter of annular groove 101 engaged therein but is larger than the inner diameter of bushing walls 85. Also, the nominal inside diameter of bushing walls 85 is slightly larger than corresponding outer diameter of post 86 for establishing a clearance between the post and the bushing for the free rotation of bristle unit 8. This configuration prevents the bristle unit dislodged from the post. During brushing, the brushing pressure pushes bristle unit 8 against the post 86, therefore, the rotary bristle unit cannot detach from the post under the brushing condition. For the oscillation of the rotary bristle unit 8, as shown in FIG. 1a, FIG. 1b and FIG. 2, a U-shaped pivotal cam linkage 242 having stud shaft 230 and L-shaped cylindrical rod 34 is engaged with the offset cylindrical rod 234 of the cap 226 which is attached to the end of first drive shaft 216. The cam linkage 242 is pivotal against stud shaft 230 which is rotationally supported by the platform 72. The cylindrical rod 34 is engaged with the notch 88 such that the pivoting motion of the cam linkage 242 imparts the oscillation of the cylindrical rod 34 and bristle unit 8 when the cam linkage is driven by the offset cylindrical rod of cap 226, which is mounted on the top end of first drive shaft 216. The first drive shaft 216 is engaged with second drive shaft 236 which is driven by motor 212. The bottom end of first drive shaft 216 has a non-circular prong-adapter 62 inserted onto the drive-socket receptacle end 64 of second drive shaft 236. In one embodiment both prong-adapter 62 and receptacle-end 64 have square-shaped cross-section. When the motor is energized, the engagement of drive shafts 236 and 216 imparts the oscillating motion of the first bristle unit 8.

The communication and engagement of the first drive shaft 216 with second drive shaft 236 is enabled by the mounting of the replaceable dual-channel brush head on the dual-channel connector 151 of the handle 4. FIG. 3a and FIG. 3b show views of detached replaceable brush head 20 and exposed connector 151. The replaceable dual-channel brush head 20 consists of platform 72 having post 86 and a spout opening 114, dual-channel neck 19 having first drive shaft 216 in first drive channel 104 and first flow channel 102 which extends to spout opening 114. The top end of dual-channel neck 19 is connected to platform 84 and the bottom end is for detachably mounting on dual-channel connector 151 of handle 4. Connector 151 has second drive shaft 236 in second drive channel 202 for coupling with first drive shaft 216, and second flow channel 204 for detachably connecting to first flow channel 102 of brush head 20.

For preventing leaking of dentifrice material, the inner attachment walls 153 of first flow channel 102 and the inner attachment wall 155 of first drive shaft channel 104 at the bottom of the brush head 20 are in intimate sliding contact with the outer wall 159 of the connector 151 when the brush head 20 is fully mounted on the connector 151. The precision of the mounting ensures the insertion of the prong-adapter 62 onto the mating receptacle end 64 of second drive shaft 236.

Referring to FIG. 1a, for dispensing dentifrice material, the flow path from the cartridge 124, which as a reservoir stores dentifrice material, through the pump chamber 94 and the flow channel 102 to the spout opening 114 and to the top of bristles in the second bristle unit 9 is full of dentifrice material (not shown). A detailed description of the pump mechanism using an elastic compressible button is given in U.S. Pat. No. 6,434,773. Here a brief description is given below. When the elastic compressible button 96 is depressed, the dentifrice material is forced to move from pump chamber 94, through flow channel 102 and spout opening 114, to the top of the second bristle unit 9. The vacuum created in chamber 94 when the pumping force is released and elastic compressible button 96 being restored to its original free position, causes dentifrice material to flow from cartridge 124 through one-way check valve 122 and into chamber 94 to replace the quantity of dentifrice material removed from the chamber by the application of the pumping force. The flow of dentifrice material from cartridge 124 causes corresponding advancement of follower 126 at the base of the cartridge. When all of the dentifrice material is depleted from cartridge 124, the cartridge is removed from the handle and replaced by a full cartridge. Cartridge 124 is fastened by threads at the base of the one-way check valve 122.

Figure 4A:
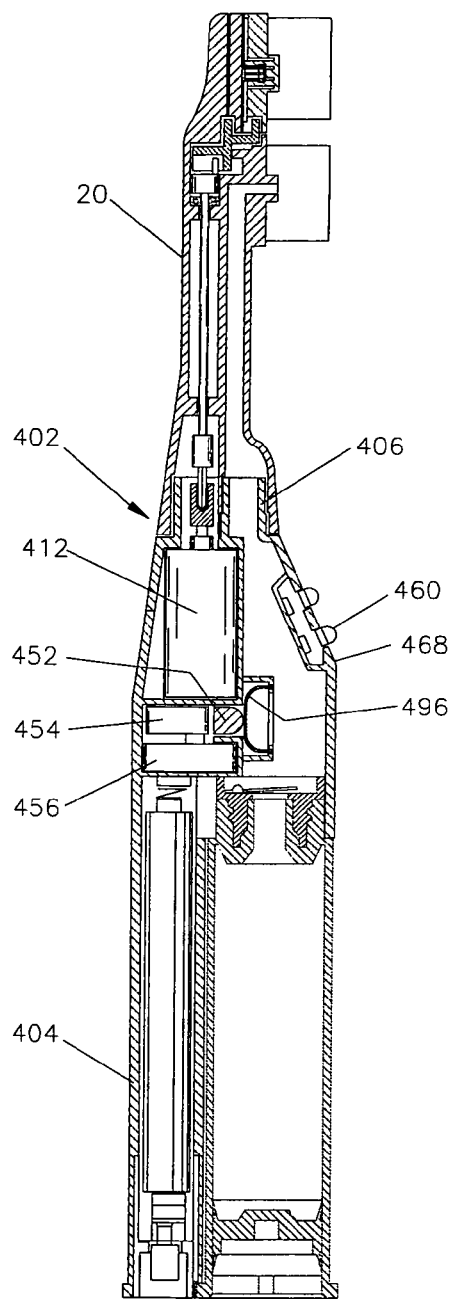
FIG. 4a is a cross section view of an electrical dentifrice dispensing toothbrush with the plunger in the non-dispensing position.
Figure 4B:
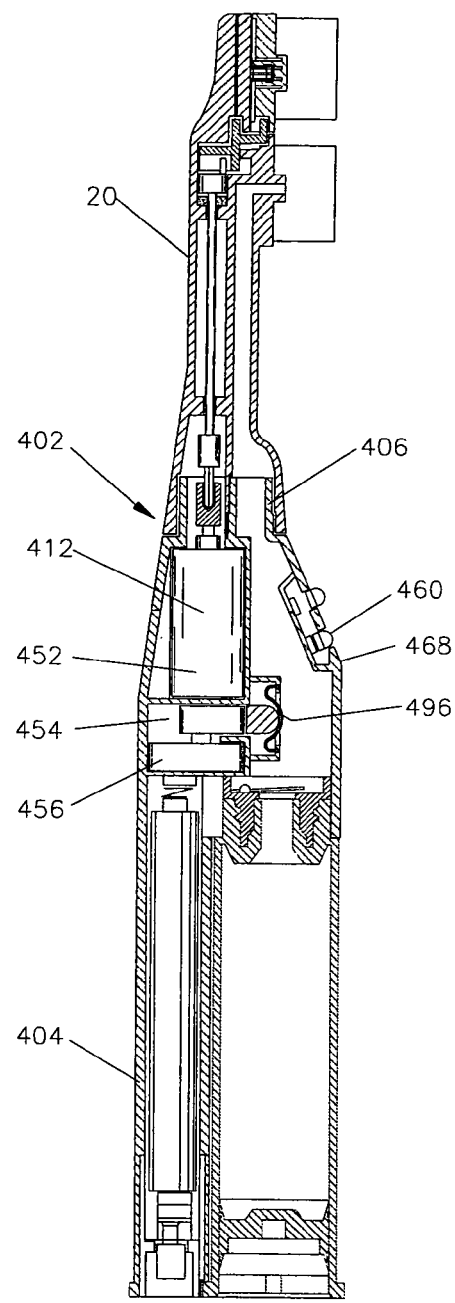
FIG. 4b is a cross section view of an electrical dentifrice dispensing toothbrush with the plunger in the dispensing position.

Another embodiment of the present invention is a dentifrice-dispensing electrical toothbrush using an electrical means to dispense the dentifrice material from the handle to the top of bristles. As shown in FIG. 4a and FIG. 4b, dentifrice-dispensing electrical toothbrush 402 has handle 404, connector 406 and replaceable dual-channel brush head 20. The structures and functions of the dual-channel brush head, the connector and the coupling of the brush-head drive shaft to the motor drive shaft are the same as shown in FIG. 1a and described previously.

However, the delivery of dentifrice material is achieved by using an electrical-mechanical means that has been disclosed in details in U.S. Pat. No. 6,735,803 by Kuo. Here the electrical-mechanical means is briefly described as follows. The electrical-mechanical means consists of rotary solenoid 456, cam 454, and plunger 452 for contacting on resilient compressible button 496 as shown in FIG. 4a, which shows these components at the non-dispensing home positions. Upon activating rotary solenoid 456 by pushing on electrical button switch 460 positioned on the external surface 468 of handle 404, cam 454 on the shaft of the rotary solenoid 456 rotates 180 degree from the non-dispensing home position to move plunger 452 forward to depress on compressible button 496 to the fully compressed dispensing position, which is shown in FIG. 4b. The compression of the resilient compressible button provides the pumping force to dispense the dentifrice material. FIG. 4b shows cam 454, plunger 452 and resilient compressible button 496 at the dispensing positions. Then upon the release of button switch 460, through a control circuitry (not shown) rotary solenoid 456 is energized to cause cam 454 to return to the home position. On the way to the home position the compressible button restores to its original shape together with the movement of the dentifrice material from the cartridge to replenish the pump chamber. Although the use of a rotary solenoid is preferred, the actuation of the plunger for compressing on the elastic button can be achieved by linear solenoid or a clutch connected to motor 412.

Figure 5:
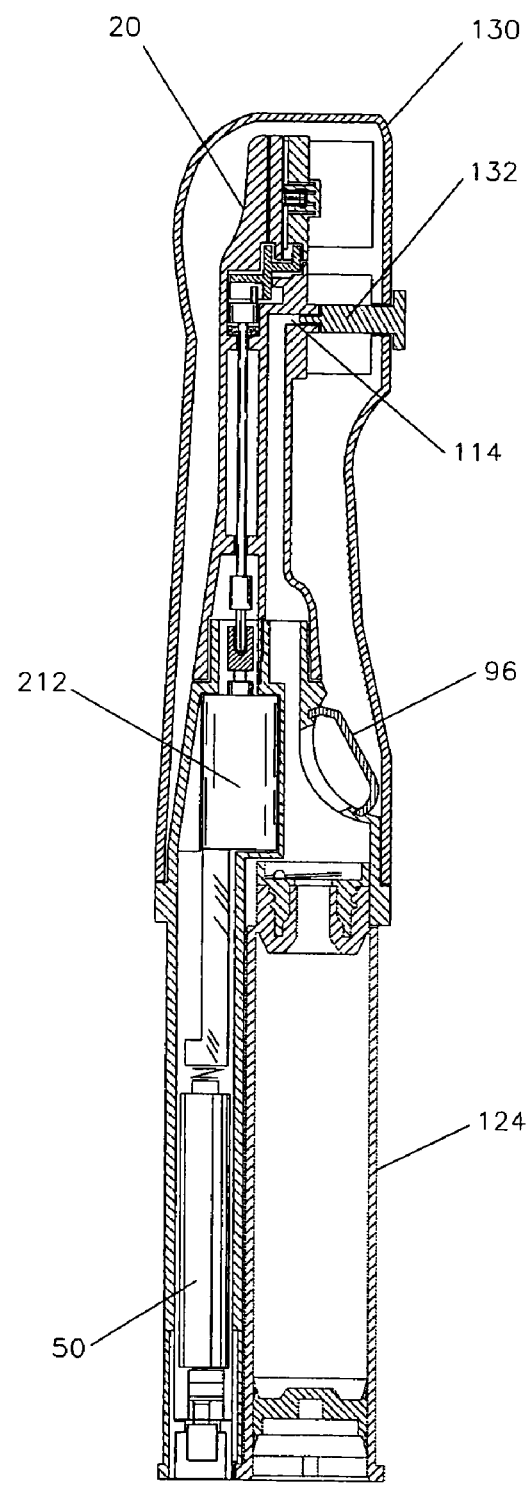
FIG. 5 is a cross section view of a dentifrice dispensing electrical toothbrush with a cover and a plug attached.

Additionally, the spout opening 114 in the dual-channel brush head 20 needs to be plugged for preventing drying of the dentifrice material. Sealing of spout opening 114 of the dentifrice dispensing electrical toothbrush is similar to that described in U.S. Pat. No. 6,434,773 by Kuo. FIG. 5 shows sealing plug 132 being inserted into spout opening 114. The positioning of the plug for sealing is facilitated by guides (not shown) on cover 130 when the cover is at its fully closed and locked position on the shoulder of the handle.

The invention has been described in detail with reference to preferred embodiments thereof. However, it is understood that variations and modifications can be effected within the spirit and scope of the invention.

I claim:

1. A dentifrice dispensing electrical toothbrush comprising:
   a. a handle having a motor, a reservoir for storing dentifrice material and a pumping means for pumping dentifrice material from the reservoir;
   b. a replaceable dual-channel brush head having:
      i. a platform with top and bottom surfaces and a post which extends from the top surface;
      ii. a dual-channel neck having a top end connected to said platform, said dual-channel neck having a first flow channel and a first drive-shaft channel housing first drive shaft;
      iii. a first rotary bristle unit having a side wall with a notch and being freely mounted on said post and driven by the first drive shaft;
      iv. a second bristle unit attached to said platform having a spout opening in communication with the first flow channel;
   c. a dual-channel connector extending from the handle having a second flow channel and a second drive-shaft channel housing a second drive shaft, said second drive shaft being connected to the motor and detachably engaged with the first drive shaft, and said second flow channel being detachably engaged with the first flow channel and in communication with the reservoir;

d. means for imparting an oscillating motion to the first rotary bristle unit through the engagement of the first drive shaft with the second drive shaft.

2. The dentifrice dispensing electrical toothbrush of claim 1 in which the means for imparting an oscillating motion to the first brush unit comprises a pivotal cam linkage having a cylindrical rod mateable with the notch in the side wall of said first bristle unit and being in communication with the first drive shaft.

3. The dentifrice dispensing electrical toothbrush of claim 2 wherein said pivotal cam linkage being driven by an offset cylindrical rod connected to the first drive shaft.

4. The dentifrice dispensing electrical toothbrush of claim 1 in which said pumping means includes an elastic, compressible button for supplying a pumping force for dispensing the dentifrice material to the spout opening.

5. The dentifrice dispensing electrical toothbrush of claim 4 in which the elastic, compressible button is pressed by an actuator when an electric switch is activated and said elastic and compressible button is released from the actuator when the electric switch is deactivated.

6. The dentifrice dispensing electrical toothbrush of claim 4 in which said pumping means includes an one-way valve, said valve is forced to close when the elastic, compressible button is depressed and the valve is forced to open when the button is released.

7. The dentifrice dispensing electrical toothbrush of claim 1 wherein said first rotary bristle unit including an annular groove positioned on inner surface of a split bushing wall, and said post having a protruding split annular rim for engaging with said annular groove with clearance for free rotation of said first rotary bristle unit.

8. The dentifrice dispensing electrical toothbrush of claim 1 wherein said reservoir is a replaceable cartridge having a moveable piston in sliding contact with the inner wall of the cartridge.

* * * * *